(12) United States Patent
Woo

(10) Patent No.: US 9,124,776 B2
(45) Date of Patent: *Sep. 1, 2015

(54) SYSTEMS AND METHODS FOR DOCUMENTING ELECTRONIC MEDICAL RECORDS RELATED TO ANESTHESIA

(75) Inventor: Shihchung Albert Woo, Boston, MA (US)

(73) Assignee: PLEXUS TECHNOLOGY GROUP, LLC, Jackson, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 13/160,833

(22) Filed: Jun. 15, 2011

(65) Prior Publication Data

US 2011/0306926 A1   Dec. 15, 2011

Related U.S. Application Data

(60) Provisional application No. 61/354,896, filed on Jun. 15, 2010.

(51) Int. Cl.
| | |
|---|---|
| H04N 7/18 | (2006.01) |
| G06F 3/0488 | (2013.01) |
| G06F 19/00 | (2011.01) |
| G06Q 10/10 | (2012.01) |
| G06Q 50/24 | (2012.01) |

(52) U.S. Cl.
CPC ................ *H04N 7/18* (2013.01); *G06F 3/0488* (2013.01); *G06F 19/3406* (2013.01); *G06F 19/3418* (2013.01); *G06F 19/3481* (2013.01); *G06Q 10/10* (2013.01); *G06Q 50/24* (2013.01); *A61M 2205/3561* (2013.01); *A61M 2205/3569* (2013.01); *A61M 2205/3576* (2013.01); *A61M 2205/502* (2013.01)

(58) Field of Classification Search
CPC ............. A61B 19/5225; A61B 5/0002; A61B 5/1113; A61B 5/743; A61M 2205/505; A61M 2205/3561
USPC ............................................... 604/65; 348/77
See application file for complete search history.

(56) References Cited

U.S. PATENT DOCUMENTS

| | | | | |
|---|---|---|---|---|
| 2004/0008223 | A1* | 1/2004 | Britton et al. | 345/762 |
| 2006/0079752 | A1* | 4/2006 | Anderl et al. | 600/407 |
| 2007/0132597 | A1* | 6/2007 | Rodgers | 340/573.1 |
| 2011/0305376 | A1* | 12/2011 | Neff | 382/128 |

* cited by examiner

*Primary Examiner* — Aarti B Berdichevsky
(74) *Attorney, Agent, or Firm* — Ropes & Gray LLP

(57) ABSTRACT

A system that displays a user interface for medical personnel to monitor and/or control the delivery medications such as anesthesia to a patient during a medical procedure. The system may gather patient data and other information from one or more patient monitors, one or more remote patient record information systems, one or more remote medical databases, and analyze various data to provide information for or to enable control of the administration of at least one medication or drug to a patient during a medical procedure such as an operation.

21 Claims, 14 Drawing Sheets

FIG. 13

SYSTEMS AND METHODS FOR DOCUMENTING ELECTRONIC MEDICAL RECORDS RELATED TO ANESTHESIA

CROSS-REFERENCE TO RELATED APPLICATIONS

This application claims the benefit of U.S. Provisional Application 61/354,896 filed on Jun. 15, 2010, the entirety of which is incorporated herein by reference.

BACKGROUND

Patient monitoring systems are widely used in the medical field to enable healthcare providers to monitor the condition of patients. Patient monitoring systems that store patient data or interface with medical record databases may be referred to as electronic medical record (EMR) systems.

Some EMR systems automatically monitor clinical events, by analyzing patient data from an electronic health record to predict, detect and potentially prevent adverse events. Patient data may include discharge/transfer orders, pharmacy orders, radiology results, laboratory results and any other data from services or healthcare provider notes.

An electronic medical record is typically a computerized legal medical record created in an organization that delivers care, such as a hospital or doctor's office. Electronic medical records are often part of a local stand-alone health information system that allows storage, retrieval and manipulation of records.

Existing EMR systems are susceptible to inefficient data entry, inaccurate or incorrect data entry, and tend to distract medical personnel during data entry, especially during critical medical procedures. Accordingly, there is a need to enhance to ability of healthcare providers to more efficiently monitor and control the administration of treatments to medical patients while also performing healthcare data recording.

SUMMARY

The application, in various embodiments, addresses the deficiencies of current patient monitoring and management systems by providing systems and methods including a patient management system that enables a caregiver, e.g., anesthesiologist, to more efficiently administer medications while monitoring a patient's status during a medical procedure, such as an operation.

In certain aspects, a system, such as a computer system, displays a user interface for medical personnel to monitor and/or control the delivery medications such as anesthesia to a patient during a medical procedure. The system may gather patient data and other information from one or more patient monitors, one or more remote patient record information systems, one or more remote medical databases, and analyze various data to provide information for or to enable control of the administration of at least one medication or drug to a patient during a medical procedure such as an operation. The system may gather information during an operation and generate data for an interoperative medical record.

The system may also provide gathered or generated patient data to other medical systems (e.g., patient records, billing, and the like). The system user interface (e.g., GUI) may include user input and information output features that enhance the user's (e.g., anesthesiologist) ability to monitor a patient and control the delivery of medical treatment to the patient. The system may interface with other medical systems such as a hospital patient data system, hospital billing system, doctor billing system, or insurance provider system. The system may gather information from other systems or deliver data recording a medical procedure to another medical record system.

The system may analyze or process certain data being collected so that the quality of the collected data is enhanced, by for example removing redundant data (artifacts) or eliminating irrelevant data so that the system user's time can be more efficiently directed to monitoring the patient. The system may use certain charts or tables and a touch screen to enable convenient user access to data in various portions of the chart. For example, the user interface display may provide a chart that includes intersecting lines (horizontal and vertical) as a user touches the display to more clearly show the user which cell of a chart to be selected.

The system may interface with a video camera and provide a view of a patient on a portion of the user interface to enable the user (e.g., healthcare provider) to monitor the patient while interfacing with the system, e.g., charting patient data. The system may use various information to control the delivery of medication/drugs to a patient, or to identify drug interaction or allergy issues for a patient. The system may synchronize data from multiple sources. The system may use access control (e.g., biometric authentication) to ensure that only authorized personnel have system access a tandem DMS device advantageously includes first and second DMS filters that utilize separation mechanisms based on two different separation models.

More particularly, in certain aspects, the systems and methods described herein include patient monitoring systems. The patient monitoring systems may include at least one patient monitoring device for monitoring a physical condition of a patient in an operating room and a video device for capturing a video image of the patient and transmitting video data associated with the video image. The patient monitoring systems may include a controller unit having a communication interface and a user interface. In certain embodiments, the communication interface may be configured with circuitry for communicating with the at least one patient monitoring device and the video device. The user interface may include a display for displaying patient data and the video image of the patient to a user, and a user input device for receiving at least one of instructions and data from the user. In certain embodiments, the video image of the patient is positioned on the display to enable the user to monitor the visual status of the patient while entering instructions or data via the input device. The user interface may be configured to display at least one of the patient data and the video image as an overlay over another visual element on the display.

In certain embodiments, the patient monitoring systems include a plurality of patient monitoring devices, each in communication with the controller unit. One or more patient monitoring devices may include a physiological monitors configured to measure at least one of heart rate, respiratory rate, blood pressure, oxygen saturation, SpO2, EEG, and the ECG. Generally, the patient monitoring device may be in wireless and/or wired communication with the controller unit and/or the user interface. The patient monitoring device may also be in wired/wireless communication with a remote device such as a laptop, PDA, or smartphone, or another type of computing device, such as a desktop personal computer. The remote device may, include among others, a cellular phone, personal digital assistant (PDA), smartphone (such as the Apple® iPhone® manufactured by Apple, Inc., located in Cupertino, Calif.), and a tablet computer or a mobile touch screen computer (such as the Apple® iPad® manufactured by Apple, Inc., located in Cupertino, Calif.).

The video device may include a camera configured to view at least a portion of the patient. In certain embodiments the video device includes a plurality of cameras, each configured to view at least a portion of the patient. Such embodiments may include a plurality of cameras that are arranged to view different portions of the patient. For example, three cameras may be used whereby, one camera is arranged to view the head portion, another camera is arranged to view the torso portion and another camera is arranged to view a leg portion of the patient. Video images from each of the plurality of cameras may be transmitted from the video device simultaneously or in sequence, as desired. Video images may be transmitted by the video device as a video stream. In certain embodiments, the video device includes a single multi-sensor camera capable of viewing the entire patient and transmitting panoramic images of the entire patient.

In certain embodiments, the video device includes hardware and software components configured to perform one or more of panning, tilting and zooming operations. In such embodiments, the controller unit may include hardware and software components for controlling these operations. When the video device includes a plurality of cameras, each camera may be configured to independently pan, tilt and zoom to view different portions of the patient. In certain embodiments, the user may control one or more operations of the video device including at least one of record, playback, pan, tilt, and zoom. In such embodiments, the user may enter one or more commands, on a user input device of the user interface, to control the operation of the video device, which in turn may be processed by the controller unit and sent to the video device. For example, the user interface may include a touch screen and the user may select on the touch screen visual elements (e.g., buttons, prompts) for selecting one or more of a plurality of cameras, the angle of the camera, pan, tilt, zoom, exposure, and recording options.

Generally, the video device may be in wireless and/or wired communication with the controller unit and/or the user interface. The video device may also be in wired/wireless communication with a remote device such as a laptop, PDA, or smartphone, or another type of computing device, such as a desktop personal computer. The remote device may, include among others, a cellular phone, personal digital assistant (PDA), smartphone (such as the Apple® iPhone® manufactured by Apple, Inc., located in Cupertino, Calif.), and a tablet computer or a mobile touch screen computer (such as the Apple® iPad® manufactured by Apple, Inc., located in Cupertino, Calif.).

In certain embodiments, the patient monitoring system further includes an infusion device configured to deliver at least one of fluids, drugs, and medications to the patient. The infusion device may be in wireless and/or wired communication with the controller unit and/or the user interface. The controller unit may be configured to operate the infusion device based on at least one of user input received through the user input device, data received from the at least one patient monitoring device, and video image received from the video device.

The controller unit may interface with the patient monitoring device, video device, infusion device, user interface and/or one or more local or remote data systems to determine the proper dose, infusion rate, and/or other treatment control applied to the patient. The controller unit may gather and/or generate data based on data collected from one or more monitors, video devices and provide such data to a local and/or remote system. In certain embodiments, the controller unit includes a communications interface, and a user interface having a display and a user input device. The user interface may include a touch screen display that integrates the user input device and the user interface.

The controller unit may include hardware and software components for processing data received from the patient monitoring device, video device, infusion device, user interface, one or more local or remote data systems, and one or more storage devices. In certain embodiments, the controller unit includes a data processing engine for enhancing quality of data collected. In such embodiments, the data processing engine may be configured to generate one or more medical charts based on the patient data. The user interface may be configured to display the one or more medical charts to the user, and the user input device may be configured to modify, add or delete information contained in the one or more displayed charts.

The controller unit may include circuitry for receiving and synchronizing data from a plurality of sources. The data sources may be located in at least one of local and remote locations. In certain embodiments, the received data includes at least one of patient data, drug data, drug interaction data, medical studies data, healthcare data, billing data, and insurance data. The controller unit may synchronize the data in time or may organize the data in sequence of receipt.

In certain embodiments, the controller unit includes hardware and software components for collecting and storing data from one or more sources. For example, according to one feature, the controller unit may include hardware and software components to retrieve historical medical data. Such a feature allows for phantom recording of data from patient monitors and/or other medical equipment, e.g., infusion device, before an EMR may be created to enable retrieval of historical data. This feature enables the controller unit to collect information from a network of monitors and machines and store data for later retrieval. The controller unit can be used for electronic health record keeping systems that interface with patient monitors and medical equipments. The controller unit gives an EMR system the ability to retrieve historical data. In certain embodiments, if a caregiver, e.g., an anesthesia provider, forgets to launch the EMR application, he/she will have the ability to import the information automatically into the EMR system from the controller unit without having to manually import the past data.

In certain embodiments, the controller unit may include image processing hardware and software components for processing the video image or video stream received from the video device. The controller unit may be configured for processing the video image in real-time. For example, the controller unit may include hardware and software components for monitoring and tracking the patient's physical movement.

The controller unit may include hardware and software components for providing enhanced security and data encryption. For example, enhanced security may include access control, biometric authentication, cryptographic authentication, message integrity checking, encryption, digital rights management services, and/or other like security services. The security may include protocols such as IPSEC and IKE. The encryption may include, without limitation, DES, AES, RSA, and any like public key or private key based schemes.

The controller unit may further include hardware and software components for providing user access authentication. In certain embodiments, the controller unit includes an authentication engine for controlling access to the user interface. The authentication engine may be configured to perform at least one of one-step physiometric and/or biometric authentication with encryption. Instead of using a username/password challenge-based authentication, the authentication engine may use a one-step authentication process using a physiometric reader.

In certain embodiments, the patient monitoring system includes an RFID sensor in communication with the controller unit for verifying the identity of the patient. In such embodiments, the controller unit may include circuitry for matching patient data with the patient identified by the RFID sensor.

In another aspect, the systems and methods described herein include an intraoperative patient care controller unit for monitoring a patient. The patient monitoring controller unit may include a communication interface, a memory device, a processor, and a touch screen user interface. The communication interface may include hardware and software components for communicating with at least one of a patient monitoring device, video device, infusion device, and remote processing device, mobile device and storage device. The memory device may include hardware and software components for storing at least patient data obtained from the at least one patient monitoring device and video images of a patient captured by the video device. The touch screen user interface may include a display and an integrated user input device built into the display. The touch screen interface may be configured to display patient data and the video image of the patient to a user while concurrently receiving at least one of instructions and data from the user. In certain embodiments, the video image of the patient is positioned on the display to enable the user to monitor the visual status of the patient while entering instructions or data via the input device.

In other aspects, the systems and methods described herein include methods for monitoring a patient. The methods may include receiving and/or storing, at a controller unit, data representative of a physical condition of a patient, from at least one patient monitoring system, and receiving and/or storing, at the controller unit, concurrently with the data, a video image of the patient. In certain embodiments, the methods include displaying, on a touch-screen user interface, simultaneously the data and the video image, and allowing, on the touch-screen user interface, a user to provide at least one of instructions and data. According to the methods described herein, the video image of the patient may be positioned on the display to enable the user to monitor the visual status of the patient while entering instructions or data via the input device.

In certain embodiments, the methods further include generating, by the controller unit, one or more reports representative of at least one of the data representative of the physical condition of the patient and data provided by the user. The controller unit may display these reports to a user on the touch screen. In certain embodiments, the reports may be displayed as a grid with cells that may be selectable by the user. The user may view and manipulate data in the report by touching and thereby selecting a cell in the report. The user may perform any suitable operation on the report including, without limitation, selecting, editing, storing and printing the report, as desired. In certain embodiments, when the user logs in into the system, the methods include generating and displaying a report showing a list of patients scheduled to be in the operating room. When the user selects a patient's name on the screen, the controller unit may display a report representative of the physical condition of the selected patient.

In certain embodiments, the methods may include prompting the user for security verification information, and based on the user's response, restricting use of the touch-screen user interface. For example, upon initialization or start-up of the controller unit, the touch screen display may prompt the user for a username and password, or a fingerprint. The user may be granted access to the patient monitoring system once the user's credentials have been verified by the system. In another example, even after the user has gained access to use the patient monitoring system described herein, the user may be prompted for another security verification to gain access to certain other information (for e.g., personal identification information of patients). In certain embodiments, the patient monitoring system may not be in continuous use and may consequently time-out. In such embodiments, the system may require the user to re-enter credentials when resuming use of the system.

In certain embodiments, the methods may include allowing a user to input, on the touch-screen user interface, information relating to a drug to be administered to the patient, and operating an infusion device connected to the controller unit based on the user input. The display device on the user interface may be configured to display patient data, a video image of the patient and control buttons to allow a user to operate the patient monitors and video device. The user interface may further be configured to display control buttons to allow a user to operate an infusion device. According to the methods described herein, the user, attempting to administer a drug to a patient using the patient monitoring system, may be prompted on the user interface for information pertaining to the drug or the patient. The user may also be prompted for authentication information to verify that the user has the authority to administer the drug and cross-verification that the correct drug is being administered.

The patient monitoring systems described herein may be used for preoperative assessment, intraoperative patient care, postoperative patient care and/or for reporting and analysis. In particular, the patient monitoring systems described herein may be used to capture anesthesia information for preoperative evaluation including information pertaining to disease and co-morbidity, information from lab and radiology reports and communication between perioperative team members. The patient monitoring systems described herein may also be used to capture information intraoperative care including information from patient monitoring devices, video devices, infusion systems, lab and pharmacy databases, and remote databases. The patient monitoring systems described herein may be used for postoperative patient care including the preparation of pain and procedure documentation, preparation of documentation useful for postoperative rounds, billing submission, and complication tracking. The patient monitoring systems described herein may be used in reporting and analysis for generating reports, analyzing provider performance, analyzing efficiency and utilization, calculating pharmacy costs and usage and reviewing credentialing and compliance.

BRIEF DESCRIPTION OF THE DRAWINGS

The foregoing and other objects and advantages of the systems and methods described herein will be appreciated more fully from the following further description thereof, with reference to the accompanying drawings. The skilled person in the art will understand that the drawings, described below, are for illustration purposes only. The drawings are not intended to limit the scope of the applicant's teaching in any way.

FIG. 13 includes a screen image of a user interface that enables a user to perform time linking between system detected time and the user's record times according to an illustrative embodiment.

DETAILED DESCRIPTION

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

Figure 1:
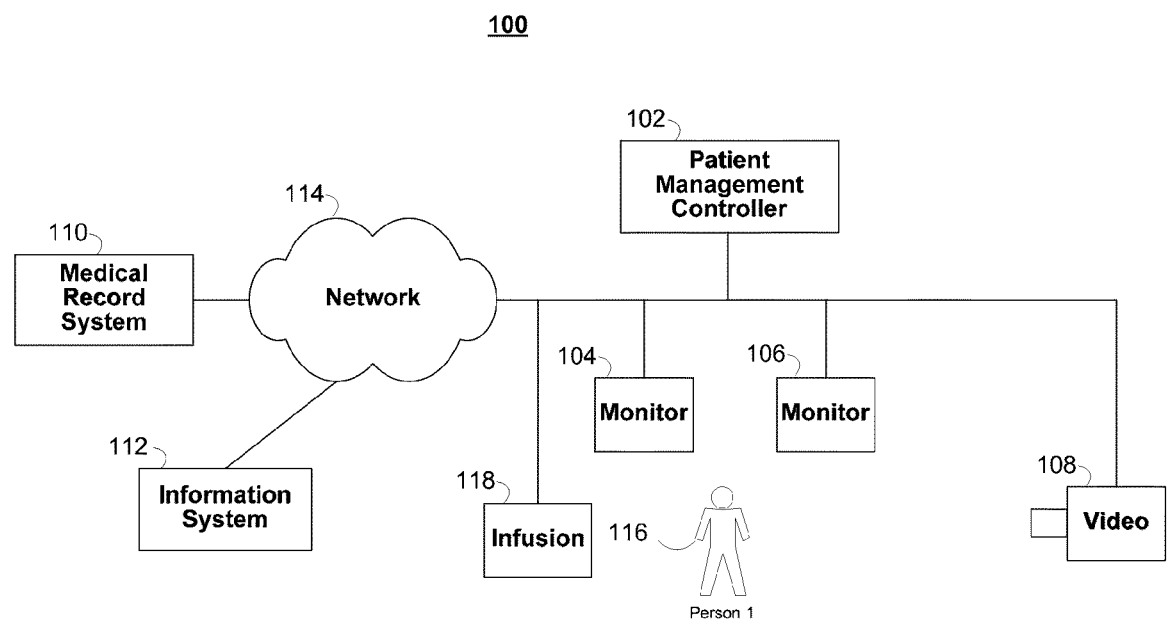
FIG. 1 includes a diagram of a system according to an illustrative embodiment.

FIG. 1 includes a diagram of an exemplary patient monitoring system 100. The patient monitoring system 100 includes a patient management controller 102, patient monitors 104 and 106, a video monitor 108, and an infusion device 118. These various components are used to monitor various physical conditions of or control the administration of a treatment to a patient 116. The controller 102 may be connected to one or more remote databases and/or systems via a network 114, such as, without limitation, a hospital record system 110 and/or a remote information system 112. The network may include a LAN, WAN, wireless network, and/or the Internet. The systems 110 and/or 112 may include EMRs or other patient-related data such as, without limitation, billing records and personal records. The systems 110 and/or 112 may include medication data, drug data, healthcare data, medical reference data, studies information, outcome data, treatment data, statistical medical data, and the like. The controller 102 may interface with one or more local or remote data systems to determine the proper dose, infusion rate, and/or other treatment control applied to the patient 116. The controller 102 may gather and/or generate data based on data collected from one or more monitors 104 or 106 and provide such data to a local and/or remote system 110 or 112.

The monitors 104 and 106 may include physiological monitors capable of sensing, without limitation, heart rate, respiratory rate, blood pressure, oxygen saturation, SpO2, EEG, ECG, and like parameters. The monitors 104 and 106 may be in communication with the controller 102 via a local area network, wireless network, or other communications mechanism. The controller 102 may interface with an infusion device 118 capable of delivery fluids, drugs, and/or medications to the patient 116. The controller 102 may monitor and/or control the rate of infusion of one or more fluids administered to the patient 116. The video device 108 may include a camera configured to view a portion of the patient 116 such as their face, head, or other portion of the patient's body. The video device 108 may be configured to send a real-time image of the patient 116 to the controller 102 for display to a user of the controller 102, e.g., an anesthesiologist.

The patient 116 may be located in a hospital, operating room, medical office, or facility for providing medical treatment. Various components of the system 100 may be co-located with the patient 116 or remotely located. For example, the monitors 104 and 106 may be located in an operating room with the patient 116 to monitor the patients condition during an operation on the patient 116. The patient management controller 102 may also be located in the operating room with the patient 116. However, the controller 102 may be positioned in the operating room such that the user of the controller 102, e.g., an anesthesiologist, does not have a direct or convenient view of the patient 116. Thus, the user of the controller 102 may rely on a video feed showing a portion of the patient 116 via a display 216 associated with the controller 102 while performing other tasks such as charting patient data and/or performing data entry. The patient 116 may be standing, laying on a bed or other platform, or in some other position.

The controller 102 may utilize data from various local or remote locations. For example, the controller may retrieve data regarding a patient from the system 110, which could include a local hospital database, and/or from system 112, which could include healthcare data located at a remote location. The various data accessible by the controller 102 may include patient data, drug data, drug interaction data, medical studies data, healthcare data, billing data, insurance data, and the like. The controller 102 may send data to various remote systems such as systems 110 and 112. The controller 102 can advantageously enable paperless and automatic data collection and/or distribution of patient data while also performing quality control checks on the collected data. In some instances, the controller 102 enables improved record keeping in support of pay for performance for insurance records and improved compliance with medical standards and/or procedures.

Various advantages of the system 100 include: 1) freeing up a caregiver, e.g., anesthesiologist, from charting by reducing the amount time and effort needed by the user to perform charting, 2) improved patient care by increasing caregiver attention to patient during a procedure, 3) improved charting and documentation by enabling automatic and/or more efficient data entry, 4) more timely data entry, 5) enabling tracking of the quality of certain information, 6) enabling more accurate recording and/or patient billing, 7) enabling enhanced uses of data such as for drug interaction analysis and use, 8) improving anesthetizing of patient body locations. The system 100 may interface with another EMR system to provide data to and/or retrieve data from the EMR system.

The system may operate in an operation room (OR) or non-OR environment. The system may collect certain patient related parameters from monitoring one or more patients that may then be used for benchmarking, identifying normal or expected parameter ranges, identifying parameter ranges associated with certain medical conditions and/or procedures, and/or for ensuring the quality assurance of medical procedures. For example, the system may be used to track and/or monitor that certain drugs were administered during appropriate procedures and/or at appropriate times during the procedure. The system may be used to determine that a procedure was performed in accordance with accepted medical standards, hospital policy, or some other requirements. The system may be used to enable administrative or other personnel to ensure that proper quality controls are adhered to during medical procedures.

Figure 2:
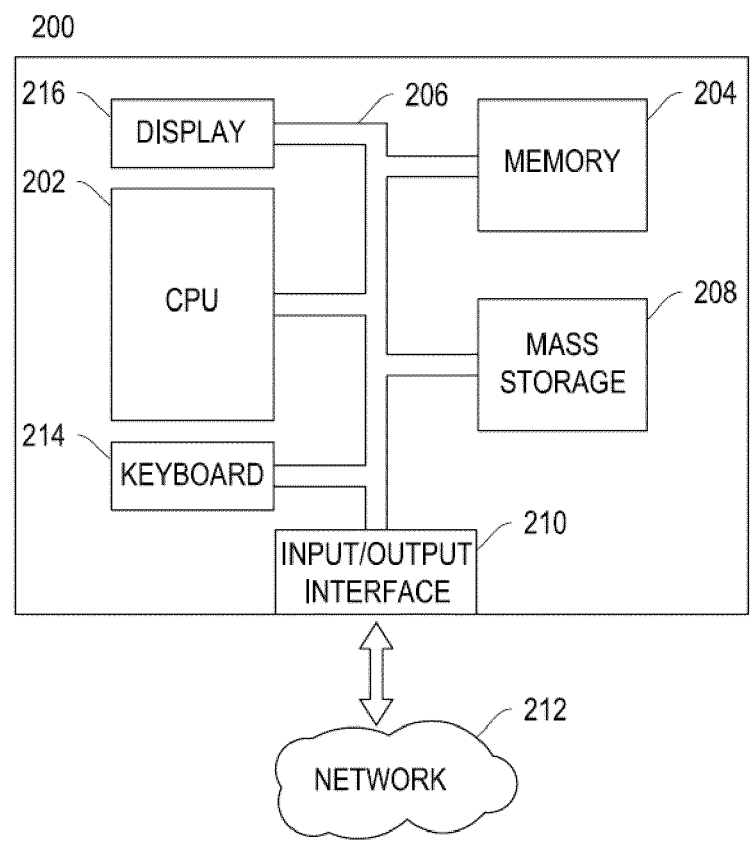
FIG. 2 includes a functional block diagram of a controller shown in FIG. 1 according to an illustrative embodiment.

FIG. 2 includes a functional block diagram of an exemplary general purpose computer system, e.g., patient management controller 200, for performing the functions of the controller 102 of FIG. 1. The exemplary computer system 200 includes a central processing unit (CPU) 202, a memory 204, and an interconnect bus 206. The CPU 202 may include a single microprocessor or a plurality of microprocessors for configuring computer system 200 as a multi-processor system. The memory 204 illustratively includes a main memory and a read only memory. The computer 200 also includes the mass storage device 208 having, for example, various disk drives, tape drives, etc. The main memory 204 also includes dynamic random access memory (DRAM) and high-speed cache memory. In operation, the main memory 204 stores at least portions of instructions and data for execution by the CPU 202.

The mass storage 208 may include one or more magnetic disk or tape drives or optical disk drives or memory sticks, for storing data and instructions for use by the CPU 202. At least one component of the mass storage system 208, preferably in the form of a disk drive or tape drive, stores the database used for processing data and/or electronic medical records of the system 100. The mass storage system 208 may also include one or more drives for various portable media, such as a floppy disk, a compact disc read only memory (CD-ROM), or an integrated circuit non-volatile memory adapter (i.e. PC-MCIA adapter) to input and output data and code to and from the computer system 200.

The computer system 200 may also include one or more input/output interfaces for communications, shown by way of example, as interface 210 for data communications via the network 212 (or network 114). The data interface 210 may be a modem, an Ethernet card or any other suitable data communications device. To provide the functions of a computer 102 according to FIG. 1, the data interface 210 may provide a relatively high-speed link to a network 212 (or network 114 of FIG. 1), such as an intranet, internet, or the Internet, either directly or through an another external interface 116. The communication link to the network 212 may be, for example, optical, wired, or wireless (e.g., via satellite or cellular network). Alternatively, the computer system 200 may include a mainframe or other type of host computer system capable of Web-based communications via the network 212. The computer system 200 may include software for operating an network application such as a web server and/or web client.

The computer system 200 also includes suitable input/ output ports or use the interconnect bus 206 for interconnection with a local display 216 and keyboard 214 or the like serving as a local user interface for programming and/or data retrieval purposes. The display 216 may include a touch screen capability to enable users to interface with the system 200 by touching portions of the surface of the display 216. Server operations personnel may interact with the system 200 for controlling and/or programming the system from remote terminal devices via the network 212.

The computer system 200 may run a variety of application programs and store associated data in a database of mass storage system 208. One or more such applications may enable the receipt and delivery of messages to enable operation as a server, for implementing server functions relating to patient management and/or information of FIG. 1.

The components contained in the computer system 200 are those typically found in general purpose computer systems used as servers, workstations, personal computers, network terminals, and the like. In fact, these components are intended to represent a broad category of such computer components that are well known in the art. For example, the components contained in the computer system 200 are those found in mobile devices such as a laptop, PDA, or smartphone. The computer system 200 may include, among others, a cellular phone, personal digital assistant (PDA), smartphone (such as the Apple® iPhone® manufactured by Apple, Inc., located in Cupertino, Calif.), and a tablet computer or a mobile touch screen computer (such as the Apple® iPad® manufactured by Apple, Inc., located in Cupertino, Calif.).

As discussed above, the general purpose computer system 200 may include one or more applications that provide patient management and information collection. The system 200 may include software and/or hardware that implements a web server application. The web server application may include software such as HTML, XML, WML, SGML, PHP (Hypertext Preprocessor), CGI, and like languages.

The foregoing embodiments of the systems and methods described herein may be realized as a software component operating in the system 200 where the system 200 is Unix workstation or other type of workstation. Other operation systems may be employed such as, without limitation, Windows, MAC OS, and LINUX. In some embodiments, the controller 102 software can optionally be implemented as a C language computer program, or a computer program written in any high level language including, without limitation, C++, Fortran, Java, or Visual BASIC. Certain script-based programs may be employed such as XML, WML, PHP, and so on. Additionally, general techniques for high level programming are known, and set forth in, for example, Stephen G. Kochan, Programming in C, Hay den Publishing (1983). The system 200 may use a DSP for which programming principles well known in the art.

As stated previously, the mass storage 208 may include a database. The database may be any suitable database system, including the commercially available Microsoft Access database, and can be a local or distributed database system. The design and development of suitable database systems are described in McGovern et al., A Guide To Sybase and SQL Server, Addison-Wesley (1993). The database can be supported by any suitable persistent data memory, such as a hard disk drive, RAID system, tape drive system, floppy diskette, or any other suitable system. The system 200 may include a database that is integrated with the system 200, however, it will be understood by those of ordinary skill in the art that in other embodiments the database and mass storage 208 can be an external element.

In certain embodiments, the system 200 may include an Internet browser program and/or be configured operate as a web server. In some embodiments, the client and/or web server may be configured to recognize and interpret various network protocols that may be used by a client or server program. Commonly used protocols include Hypertext Transfer Protocol (HTTP), File Transfer Protocol (FTP), Telnet, and Secure Sockets Layer (SSL), for example. However, new protocols and revisions of existing protocols may be frequently introduced. Thus, in order to support a new or revised protocol, a new revision of the server and/or client application may be continuously developed and released.

In certain embodiments, the system 100 includes a networked-based, e.g., Internet-based, application that may be configured and run on the system 200 and/or any combination of the other components of the system 100. The controller 102 (or system 200) may include a web server running a Web 2.0 application or the like. Web applications running on the controller 102 may use server-side dynamic content generation mechanisms such, without limitation, JavaScript, CGI, PHP, or ASP. In certain embodiments, mashed content may be generated by the web browser 144 via, for example, client-side scripting including, without limitation, JavaScript and/or applets.

In certain embodiments, the controller 102 may include applications that employ asynchronous JavaScript+XML (Ajax) and like technologies that use asynchronous loading and content presentation techniques. These techniques may include, without limitation, XHTML and CSS for style presentation, document object model (DOM) API exposed by a web browser, asynchronous data exchange of XML data, and web browser side scripting, e.g., JavaScript. Certain web-based applications and services may utilize web protocols including, without limitation, the services-orientated access protocol (SOAP) and representational state transfer (REST). REST may utilize HTTP with XML.

The controller 102 may also provide enhanced security and data encryption. Enhanced security may include access control, biometric authentication, cryptographic authentication, message integrity checking, encryption, digital rights management services, and/or other like security services. The security may include protocols such as IPSEC and IKE. The encryption may include, without limitation, DES, AES, RSA, and any like public key or private key based schemes.

Figure 3:
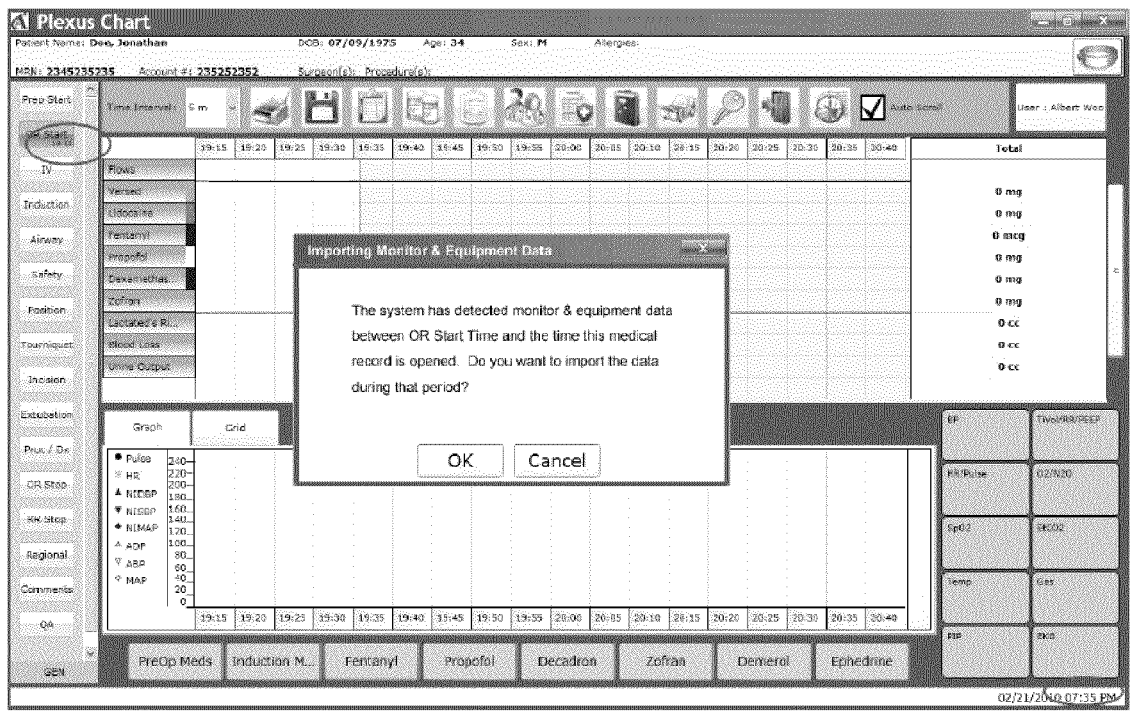
FIG. 3 includes screen image of a user interface that enables retrieval of historical medical data according to an illustrative embodiment.

FIG. 3 includes a screen image of an exemplary user interface of the controller unit that enables retrieval of historical medical data. FIG. 3 illustrates how the controller 102, in certain embodiments, enables phantom recording of Anesthesiology data from patient monitors 104 and 106 and/or other medical equipment, e.g., infusion device 118, before an EMR may be created to enable retrieval of historical data. This feature enables the system 100 to collect information from a network of monitors and machines and store data for later retrieval. The system 100 can be used for electronic health record keeping systems that interface with patient monitors and medical equipments. The system 100 and controller 102 gives an EMR system the ability to retrieve historical data. Current systems can only capture present and future data as long as a software application is running that has established a connection with the monitors and medical equipments. Thus, if a caregiver, e.g., an anesthesia provider, forgets to launch the EMR application, he/she will have the ability to import the information automatically into the EMR system from the controller 102 without having to manually import the past data.

Figure 4:
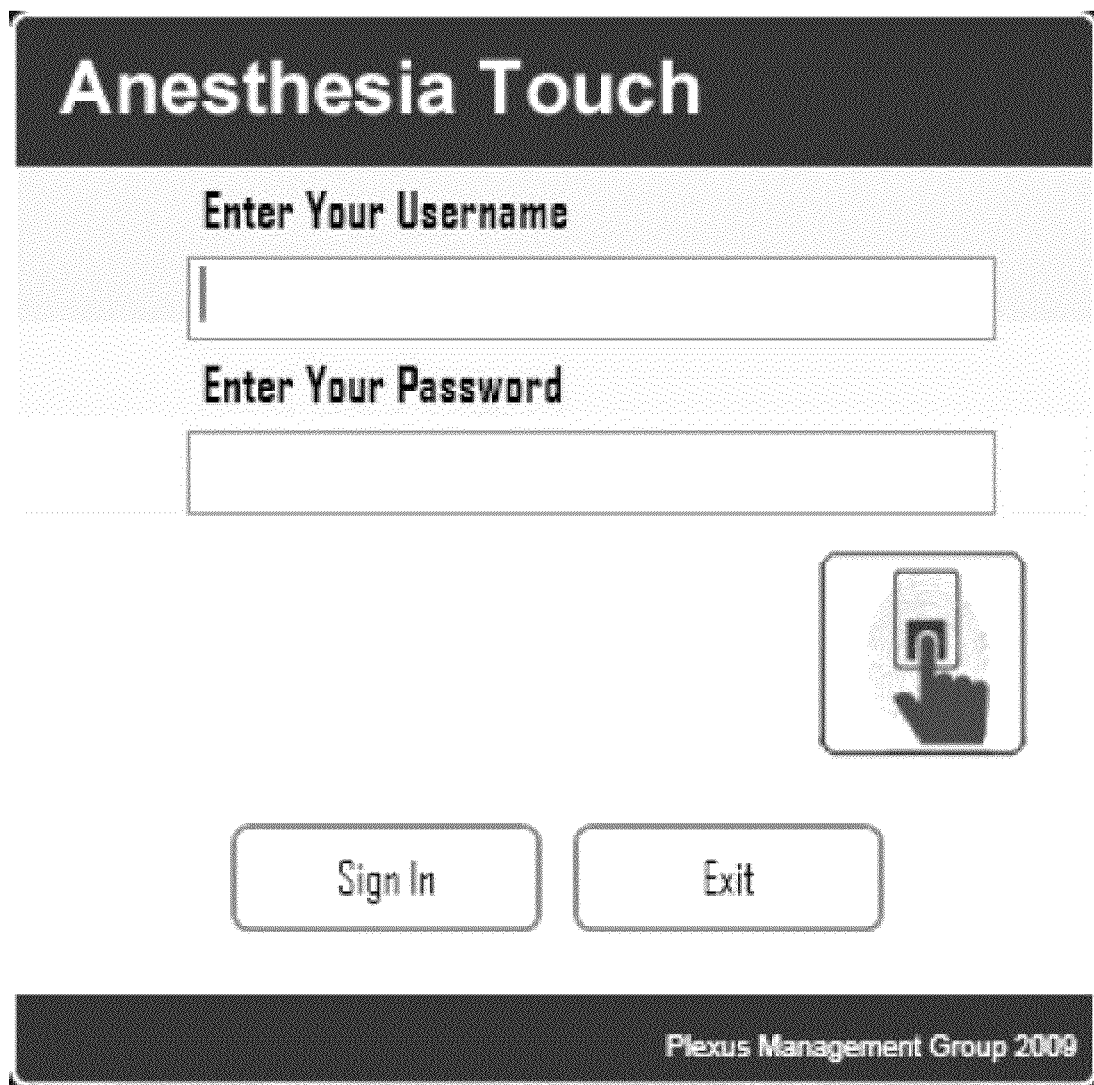
FIG. 4 includes a screen image of a user interface including user access authentication according to an illustrative embodiment.

FIG. 4 includes a screen image of an exemplary user interface including user access authentication. In one embodiment, the controller 102 enables one-step physiometric and/or biometric authentication with encryption. Instead of using a username/password challenge-based authentication, the controller 102 may use a one-step authentication process using a physiometric reader. The physiometric data may then be digitized, encrypted, and transmitted over a secure connection using certificate identification. The encryption may vary between each authentication routine and, therefore, be difficult for intruders to decipher and perform false authentication.

Figure 5:
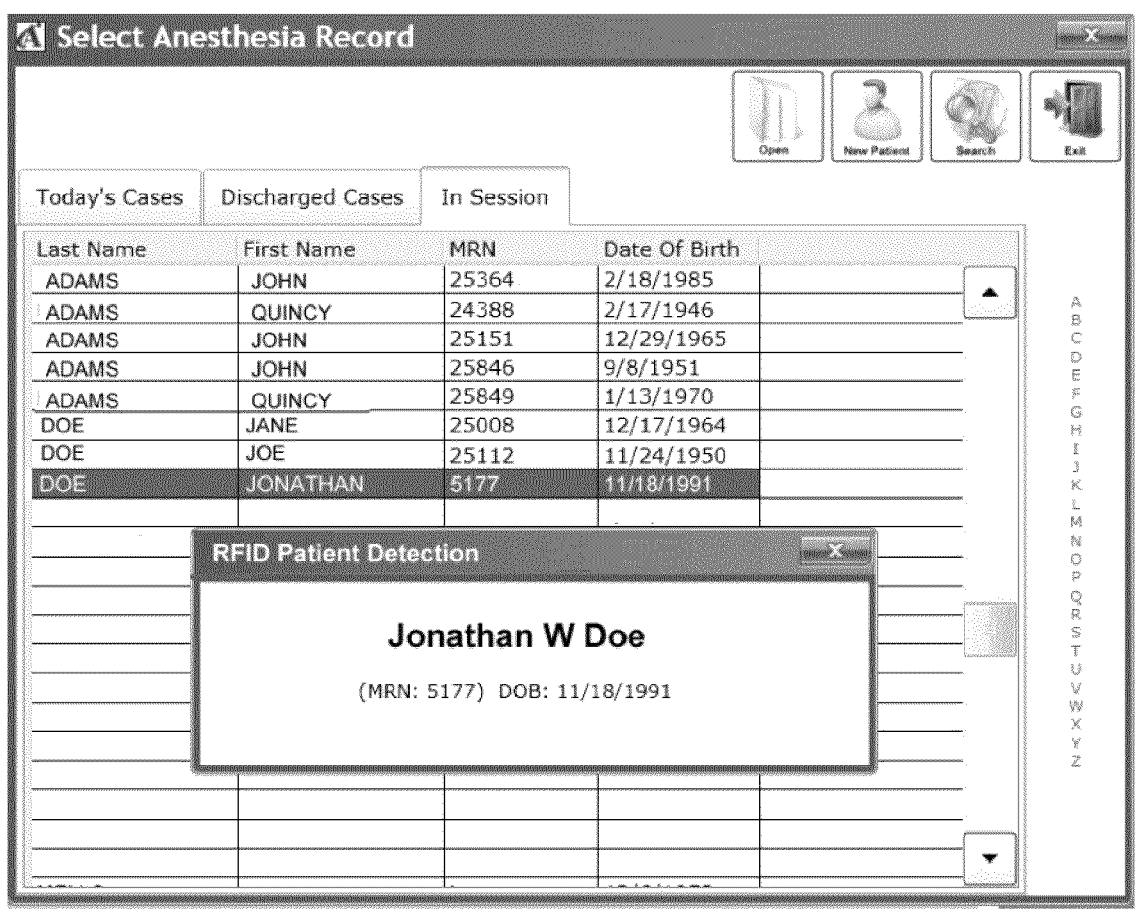
FIG. 5 includes a screen image of a user interface showing identification of a patient using an RFID sensor according to an illustrative embodiment.

FIG. 5 includes a screen image of an exemplary user interface showing identification of a patient using an RFID sensor in communication with the controller 102. In certain embodiments, the controller 102 enables patient verification integration leading to a one-step record creation. The patient management system 100 may identify the patient 116 either by barcode scanning or RFID sensors and create a new record automatically. In current systems, the user has to choose a patient from a list and open or create a record. The system 100 and/or controller 102 enables a quicker workflow by eliminating that process.

Figure 6:
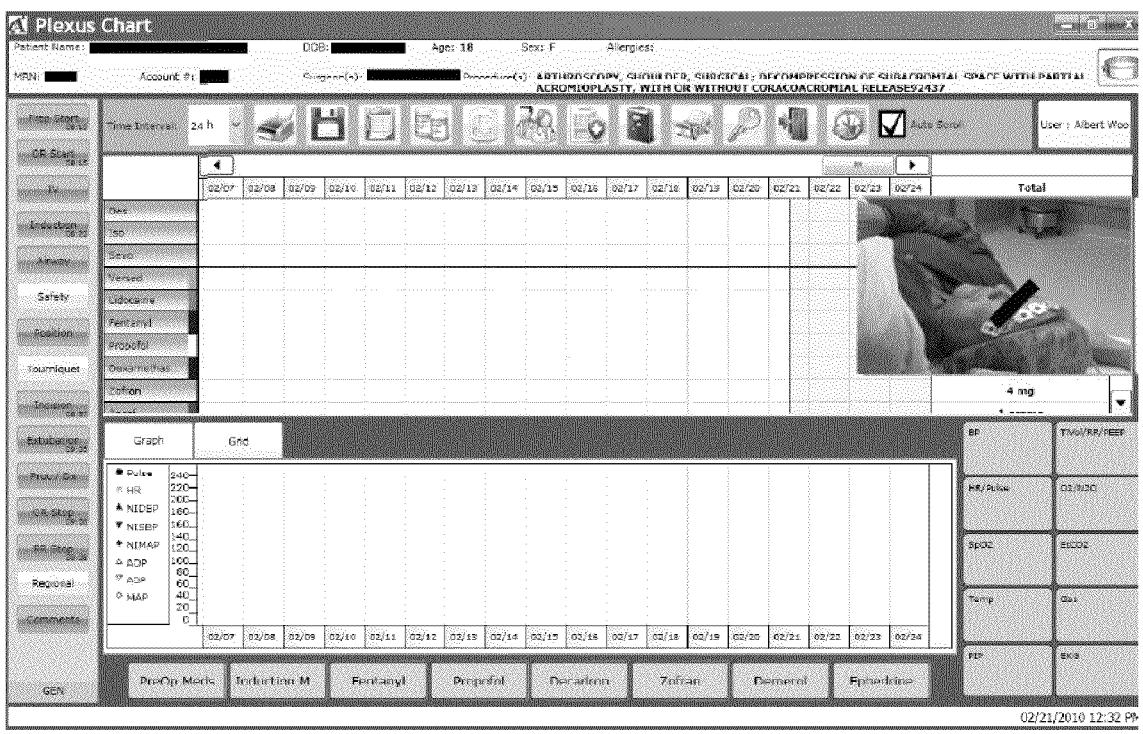
FIG. 6 includes a screen image of a user interface having a video image of a patient according to an illustrative embodiment.

FIG. 6 includes a screen image of an exemplary user interface having a video image of a patient. In certain embodiments, the system 100 enables real-time video streaming to the controller 102 to ensure adequate patient monitoring. When a clinician spends time documenting anesthesia events or using the controller 102, it is often difficult to pay attention to the patient. The present system 100 can be configured to stream video of the patient 116 onto the display 216 of the controller 102. Such a feature provides a similar advantage as the technology used in the automobiles where the speedometer data is projected onto the front wind shield glass to enhance the user's attention.

Figure 7:
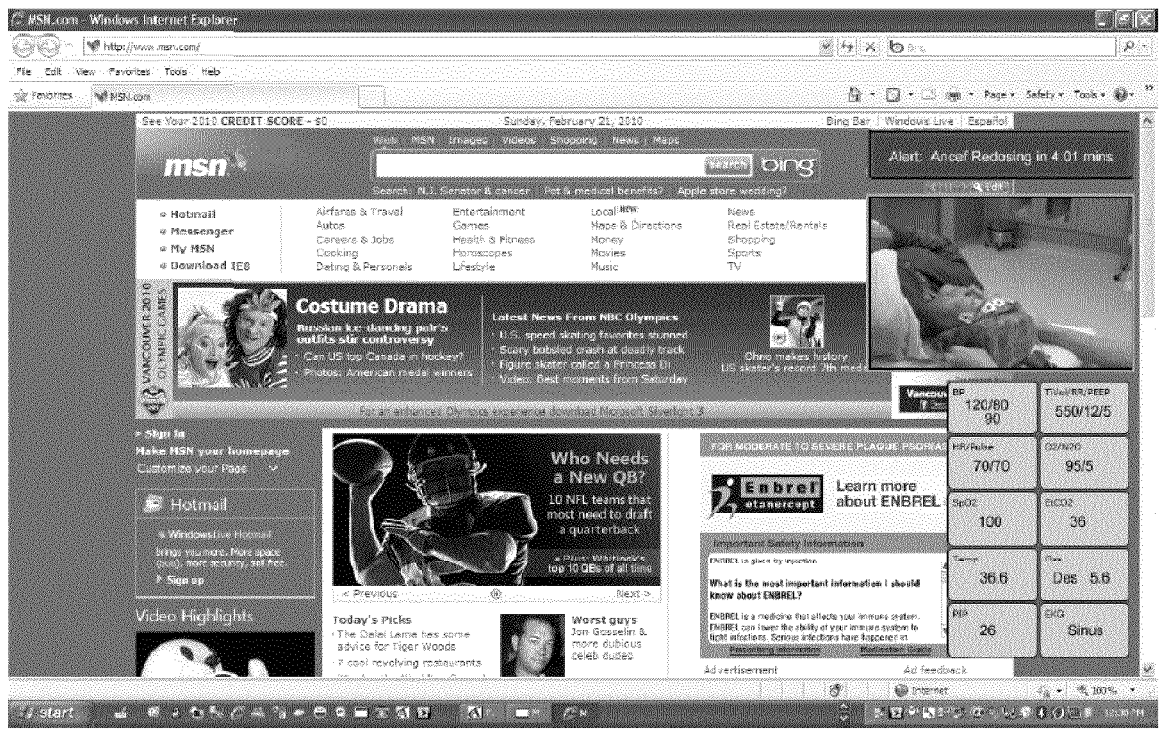
FIG. 7 includes a screen image of a user interface having an overlay of important patent data and/or patient related alerts according to an illustrative embodiment.

FIG. 7 includes a screen image of an exemplary user interface having an overlay of important patent data and/or patient related alerts. In certain embodiments, the controller 102 provides always on top alerts, live monitors, and video streaming. The controller 102 can enable important aspects of an EMR to stay on top of multiple other windows on a computer desktop running on the controller 102. The computer, e.g., controller 102, may be used for other tasks such as information lookup and medical imaging retrieval. The controller 102 enables the user to do those tasks while paying attention to the important patient 116 data during anesthesia or another medical procedure.

Figure 8:
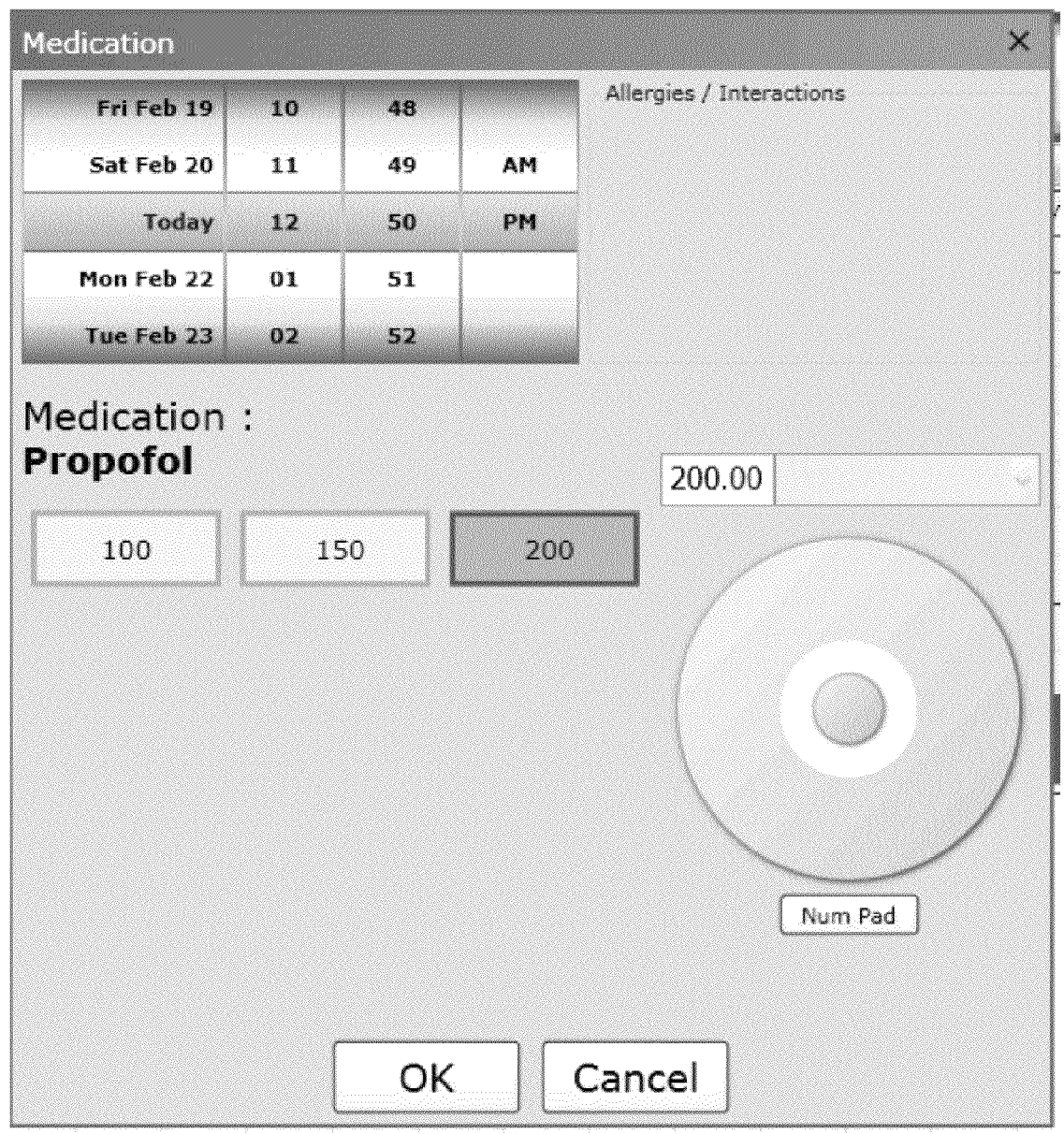
FIG. 8 includes a screen image of user interface that enable control of fluid and/or drug infusion of a patient according to an illustrative embodiment.

FIG. 8 includes a screen image of an exemplary user interface that enables control of fluid and/or drug infusion of a patient. In certain embodiments, the controller 102 includes a dial control medication and fluid entries interface via a touch screen display 216. The controller 102 may include a software application having a software control dial which is preprogrammed with specific drug information such as default, minimum dosage, maximum dosage, and/or incremental dosage. As the user spins the software control dial, the application can increment dosage and/or fluid amounts or rates according to the specific incremental range for the specific medication, up to an upper limit. A default dose can be user-dependent to enhance further customization. The application may perform other analyses such as checking for drug interaction with other drugs or patient allergies.

Figure 9:
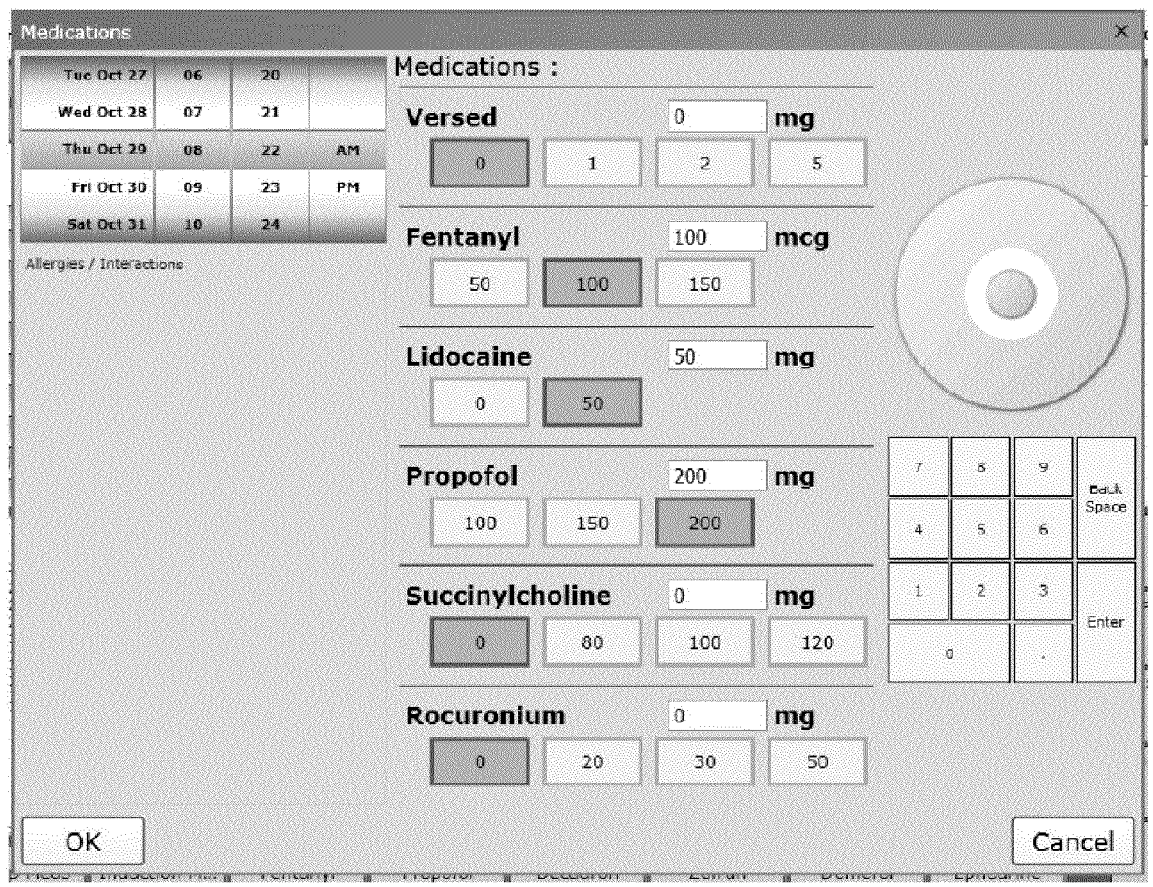
FIG. 9 includes a screen image of a user interface having smart buttons that enable efficient entry of medication or fluids information according to an illustrative embodiment.

FIG. 9 includes a screen image of an exemplary user interface having smart buttons that enable efficient entry of medication or fluids information. In certain embodiments, the controller 102 may include an interface having smart buttons. For example, the display 216 may include a touch screen capability and/or a set of controls that enable quick entry of medication or fluids information which is preprogrammed with drug info and user preferences. The controller 102 may store specific drug data along with the most usual dose as well as the user's preference dose under a certain condition.

Figure 10:
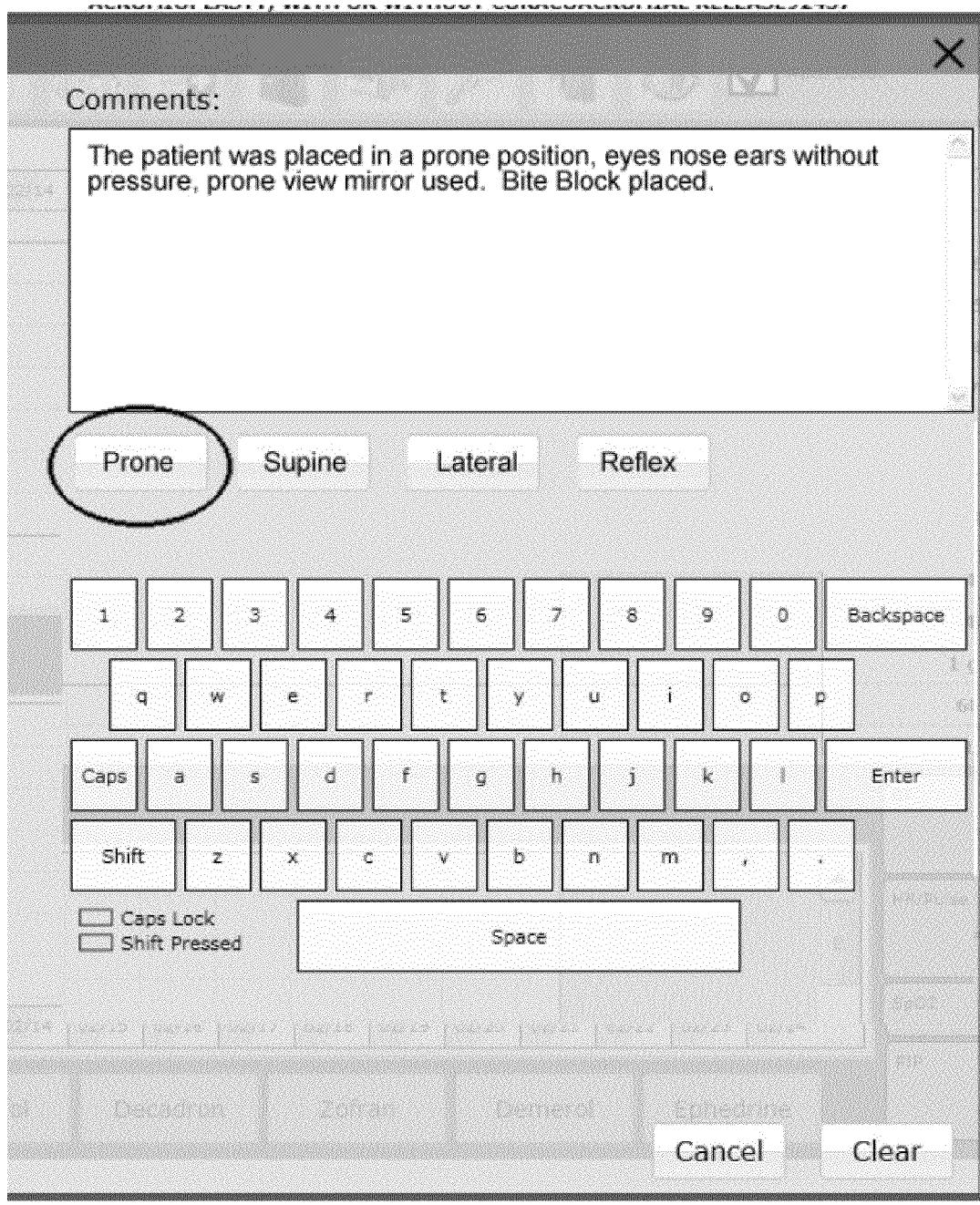
FIG. 10 includes a screen image of a user interface having a user-specific template to enable more efficient event information according to an illustrative embodiment.

FIG. 10 includes a screen image of an exemplary user interface having a user-specific template to enable more efficient event information recording. In certain embodiments, the controller 102 may include a one touch custom documentation feature. For each event that occurs during anesthesia care (or some other medical treatment), each clinician or anesthesia provider may document the event differently. Instead of limiting the users to document uniformly, the controller 102 may include a feature in which user-specific templates can be retrieved and pulled into an edit area directly along with medical coding information relevant for future analysis.

Figure 11:
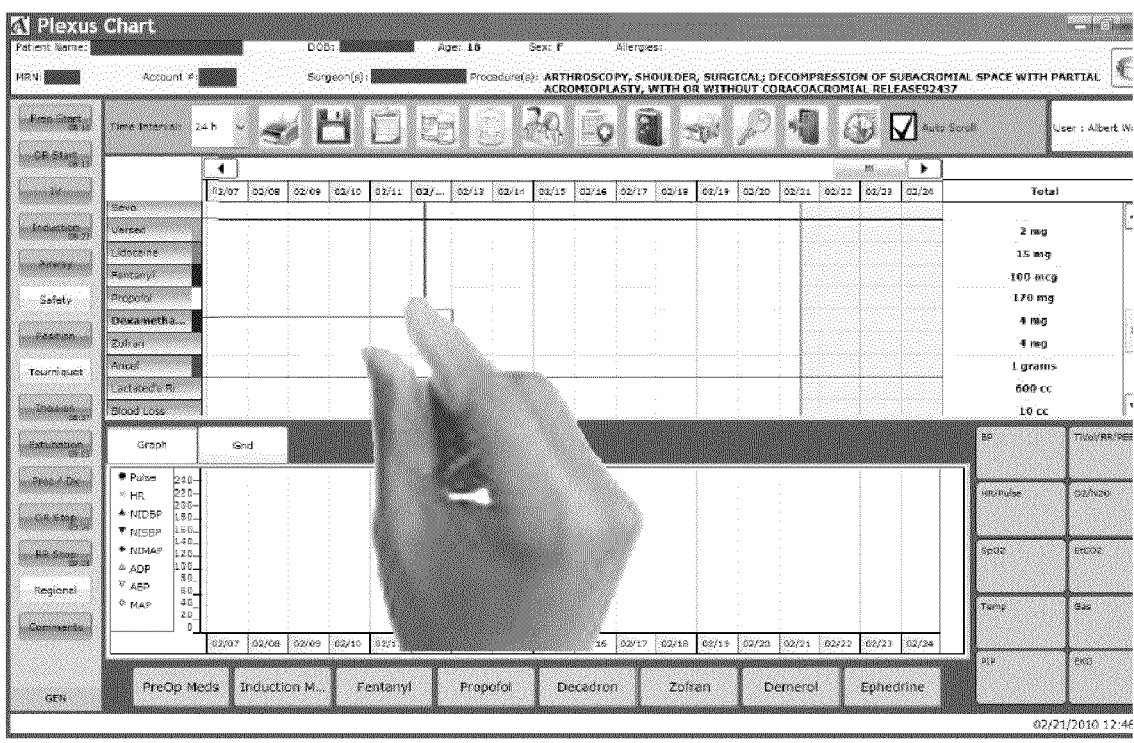
FIG. 11 includes a screen image of a user interface having a touch screen and an information grid that includes orthogonal lines to enhance a user's ability to locate the correct cell of the grid according to an illustrative embodiment.

FIG. 11 includes a screen image of an exemplary user interface having a touch screen and an information grid that includes orthogonal lines to enhance a user's ability to locate the correct cell of the grid. In certain embodiments, the controller 102 enables data charting of medication, fluids, physiologic data using a grid cell locator/positioning feature. In order to fit a lot of information onto a screen, a grid control is often used to track medication information. The problem with using a touch screen with these grids is that the user's finger is often bigger than the grid box itself which makes it difficult for the user to know which box was selected. The controller 102 may provide one or more lines, including orthogonal lines, that identify the grid location, allowing the user to more easily identify which grid cell was selected.

Figure 12:
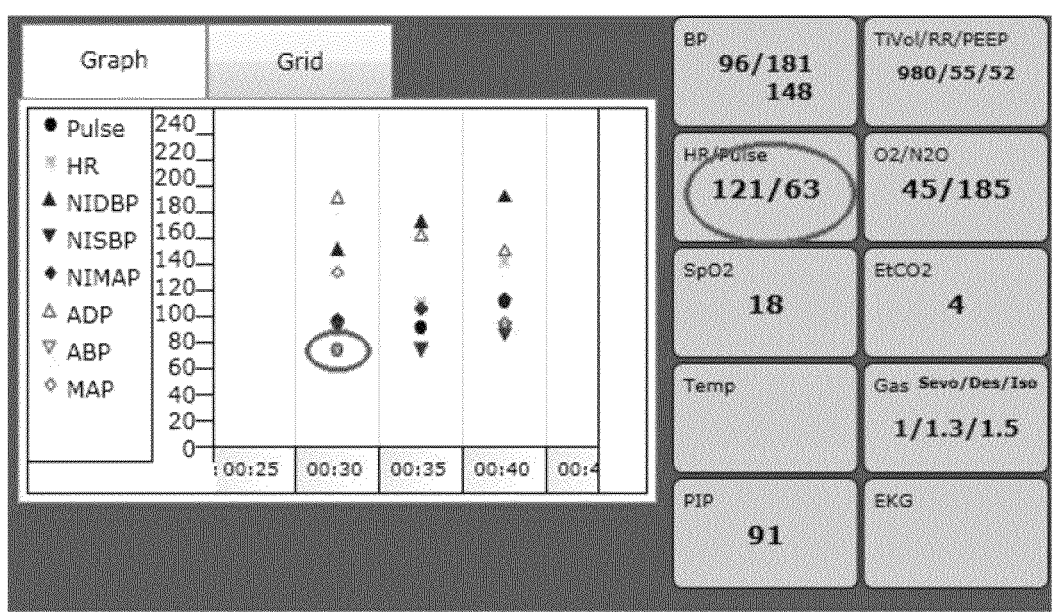
FIG. 12 includes a screen image of a user interface that enables the system to identify redundant patient data and select the more appropriate data to display according to an illustrative embodiment.

FIG. 12 includes a screen image of an exemplary user interface that enables the system to identify redundant patient data and select the more appropriate data to display. In certain embodiments, the controller 102 manages and/or processes redundant clinical information using an application including a priority algorithm. There are sometimes redundant data collected from the patient monitors 104 and 106. For example, blood pressure may be measured invasively (transducing a catheter) or noninvasively (blood pressure cuff). When the controller 102 has two sets of information that represent a somewhat similar condition, the controller can take these information and process them to determine which set should be the displayed data. The controller 102 may use a priority function where to user specifies which data should have priority. Alternatively, the controller 102 may use an algorithm that automatically determines which data form which monitors should have priority.

Figure 13:
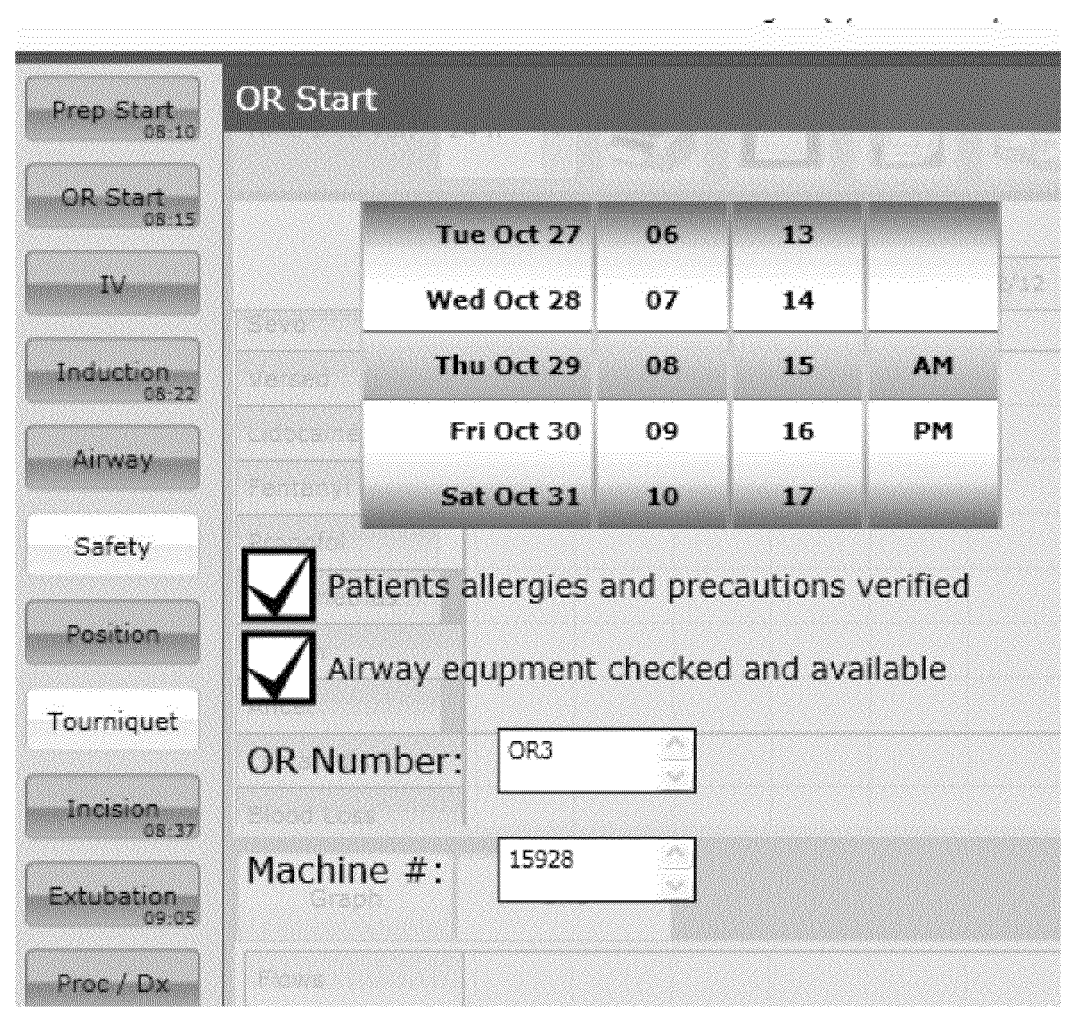

FIG. 13 includes a screen image of an exemplary user interface that enables a user to perform time linking between system-detected time and the user's record times. In certain embodiments, the controller 102 enables a predefined event timing linkage feature. When a healthcare provider is documenting his/her care for the patient 116, most events would include a time. However, it may be difficult to remember the exact timing of events. The controller 102 can suggest a time based on previous information captured from one or more time sources. For example, as a patient 116 enters the operating room, an RFID sensor can trigger documentation of that event. That time is often the same time as the operating room start time. By linking these events via the controller 102, users can fill out the time for events associated with the patient 116 treatment more efficiently.

Figure 14:
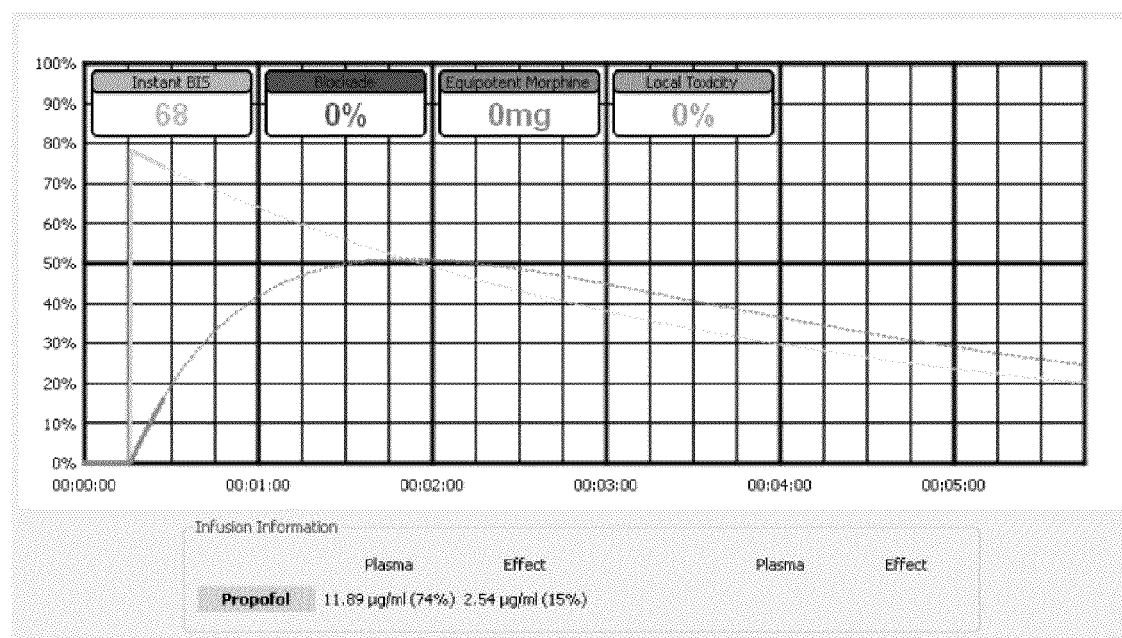
FIG. 14 includes a screen image of a user interface that provides a display of pharmacokinetic information such as plasma and target effect site concentration of medication give to a patient according to an illustrative embodiment.

FIG. 14 includes a screen image of an exemplary user interface that provides a display of pharmacokinetic information such as plasma and target effect site concentration of medication give to a patient. In certain embodiments, the controller 102 enables pharmacokinetic and/or pharmacodynamic data integration into an anesthesia EMR system. The system 100 provides a novel way to display pharmacokinetic and pharmacodynamic data within an anesthesia electronic medical record. There are currently no anesthesia EMR on the market that have the capability to display pharmacokinetic and pharmacodynamic data such as plasma and target effect site concentration of medications that are given to patients. The controller 102 may also provide additional modeling such as BIS prediction.

It will be apparent to those of ordinary skill in the art that certain aspects involved in the operation of the controller 102 may be embodied in a computer program product that includes a computer usable and/or readable medium. For example, such a computer usable medium may consist of a read only memory device, such as a CD ROM disk or conventional ROM devices, or a random access memory, such as a hard drive device or a computer diskette, or flash memory device having a computer readable program code stored thereon.

Variations, modifications, and other implementations of what is described may be employed without departing from the spirit and scope of the disclosure. More specifically, any of the method and system features described above or incorporated by reference may be combined with any other suitable method, system, or device feature disclosed herein or incorporated by reference, and is within the scope of the contemplated systems and methods described herein. The systems and methods may be embodied in other specific forms without departing from the spirit or essential characteristics thereof. The foregoing embodiments are therefore to be considered in all respects illustrative, rather than limiting of the systems and methods described herein. The teachings of all references cited herein are hereby incorporated by reference in their entirety.

The invention claimed is:

1. A patient monitoring system, comprising:
    at least one patient monitoring device for monitoring a physical condition of a patient in an operating room during an operation on the patient;
    a video device for capturing a video image of the patient during the operation and transmitting video data associated with the video image; and
    a controller unit located in the operating room and configured to control an infusion device coupled to the patient, the controller unit including
        a communication interface for communicating with the at least one patient monitoring device and the video device, and
        a user interface having a display for displaying to a user patient data and the video image of the patient during the operation, and a user input device for receiving at least one of instructions and data from the user;
    wherein the video image of the patient is positioned on the display to enable the user to monitor the visual status of the patient during the operation while entering instructions or data via the input device; and
    wherein the user interface includes a touch screen display that integrates the user input device and the display.

2. The patient monitoring system of claim 1, comprising a plurality of patient monitoring devices, each in communication with the controller unit.

3. The patient monitoring system of claim 1, wherein the at least one patient monitoring device includes physiological monitors configured to measure at least one of heart rate, respiratory rate, blood pressure, oxygen saturation, SpO2, EEG, and the ECG.

4. The patient monitoring system of claim 1, wherein the video device includes a plurality of cameras, each configured to view at least a portion of the patient.

5. The patient monitoring system of claim 1, wherein the controller unit includes an authentication engine for controlling access to the user interface.

6. The patient monitoring system of claim 1, comprising an RFID sensor in communication with the controller unit for verifying the identity of the patient.

7. The patient monitoring system of claim 1, wherein the user input device includes one or more buttons preprogrammed with at least one of drug information and user preferences.

8. The patient monitoring system of claim 1, wherein the user interface is configured to display at least one of the patient data and the video image as an overlay over another visual element on the display.

9. The patient monitoring system of claim 1, further comprising a mobile computing device having a touch screen in wireless communication with the controller unit for viewing at least one of the patient data and the video image, and for receiving at least one of instructions and data from the user.

10. The patient monitoring system of claim 1, wherein the infusion device is configured to deliver at least one of fluids, drugs, and medications to the patient.

11. The patient monitoring system of claim 10, wherein the controller unit is configured to operate the infusion device based on at least one of user input received through the user input device, data received from the at least one patient monitoring device, and video image received from the video device.

12. The patient monitoring system of claim 1, wherein the controller unit includes circuitry for receiving and synchronizing data from a plurality of sources.

13. The patient monitoring system of claim 12, wherein the received data includes at least one of patient data, drug data, drug interaction data, medical studies data, healthcare data, billing data, and insurance data.

14. A patient monitoring controller unit, comprising:
a communication interface for communicating with at least one patient monitoring device and a video device;
a memory device for storing at least patient data obtained from the at least one patient monitoring device during an operation on a patient and video images of the patient during the operation captured by the video device;
a processor; and
a touch-screen user interface, including
a display for displaying patient data and the video image of the patient to a user, and
a user input device for receiving at least one of instructions and data from the user;
wherein the video image of the patient is positioned on the display to enable the user to monitor the visual status of the patient during the operation while entering instructions or data via the input device; and
wherein the patient monitoring controller unit is configured to control an infusion device coupled to the patient.

15. The patient monitoring controller unit of claim 14, wherein the patient data includes ECG data.

16. A method of monitoring a patient, comprising:
receiving, at a controller unit, data representative of a physical condition of a patient during an operation, from at least one patient monitoring system;
receiving, at the controller unit, concurrently with the data, a video image of the patient during the operation;
displaying, on a touch-screen user interface, simultaneously the data and the video image;
allowing, on the touch-screen user interface, a user to provide at least one of instructions and data; and
operating, with the controller unit, an infusion device coupled to the patient;
wherein the video image of the patient is positioned on the display to enable the user to monitor the visual status of the patient during the operation while entering instructions or data via the input device.

17. The method of claim 16, further comprising generating, by the controller unit, one or more reports representative of at least one of the data representative of the physical condition of the patient and data provided by the user.

18. The method of claim 16, further comprising prompting the user for security verification information, and based on the user's response, restricting use of the touch-screen user interface.

19. The method of claim 16, further comprising storing, at the controller unit, data from the at least one patient monitoring system.

20. The method of claim 16, further comprising allowing the user to input, on the touch-screen user interface, information relating to a drug to be administered to the patient, and operating the infusion device based on the user input.

21. The method of claim 16, wherein the data representative of a physical condition of the patient includes ECG data.

* * * * *